(12) United States Patent
Shoureshi et al.

(10) Patent No.: US 7,716,005 B2
(45) Date of Patent: May 11, 2010

(54) SMART INSOLE FOR DIABETIC PATIENTS

(75) Inventors: Rahmat A. Shoureshi, Golden, CO (US); Stephen F. Albert, Denver, CO (US)

(73) Assignee: Colorado Seminary, which owns and operates The University of Denver, Denver, CO (US)

( * ) Notice: Subject to any disclaimer, the term of this patent is extended or adjusted under 35 U.S.C. 154(b) by 549 days.

(21) Appl. No.: 11/556,914

(22) Filed: Nov. 6, 2006

(65) Prior Publication Data
US 2008/0109183 A1 May 8, 2008

(51) Int. Cl.
*G01K 13/00* (2006.01)
(52) U.S. Cl. ........................................ 702/131
(58) Field of Classification Search ................ 702/131
See application file for complete search history.

(56) References Cited

U.S. PATENT DOCUMENTS

| | | | |
|---|---|---|---|
| 3,791,375 A | 2/1974 | Pfeiffer | |
| 4,697,360 A | 10/1987 | Sartor | |
| 4,745,930 A | 5/1988 | Confer | |
| 5,033,291 A | 7/1991 | Podoloff et al. | |
| 5,323,650 A | 6/1994 | Fullen et al. | |
| 5,357,696 A | 10/1994 | Gray et al. | |
| 5,373,651 A | 12/1994 | Wood | |
| 5,400,529 A | 3/1995 | Bell et al. | |
| 5,408,873 A | 4/1995 | Schmidt et al. | |
| 5,566,479 A | 10/1996 | Gray et al. | |
| 5,579,439 A * | 11/1996 | Khan | 706/2 |
| 5,642,096 A | 6/1997 | Leyerer et al. | |
| 5,678,448 A | 10/1997 | Fullen et al. | |
| 5,929,332 A * | 7/1999 | Brown | 73/172 |
| 6,033,370 A | 3/2000 | Reinbold et al. | |
| 6,122,846 A | 9/2000 | Gray et al. | |
| 6,195,921 B1 | 3/2001 | Truong | |
| 6,382,029 B1 | 5/2002 | Shoureshi et al. | |

(Continued)

FOREIGN PATENT DOCUMENTS

EP     0522882 A2     1/1993

(Continued)

OTHER PUBLICATIONS

American Diabetes Association (Aug. 1999), Consensus Development Conference on Diabetic Foot Wound Care, Boston, Massachusetts, Apr. 7-8, 1999, *Diabetes Care* 22(8):1354-1360.

(Continued)

*Primary Examiner*—Drew A Dunn
*Assistant Examiner*—Stephen J Cherry
(74) *Attorney, Agent, or Firm*—Greenlee, Winner and Sullivan, P.C.

(57) ABSTRACT

This invention is a temperature-based smart insole capable of continuously or intermittently measuring the foot temperature of the patient at one or more locations of the foot while the insole is worn. The device provides feedback to the patient alerting the individual of risk based on his/her plantar temperatures. Benefits of this device include: its ability to free the patient from the clinical setting and increase patient's confidence to be mobile, thus enhancing circulation while at the same time allowing the patient to self-monitor their feet.

26 Claims, 6 Drawing Sheets

U.S. PATENT DOCUMENTS

| | | |
|---|---|---|
| 6,836,744 B1 | 12/2004 | Asphahani et al. |
| 6,978,684 B2 | 12/2005 | Nurse |
| 7,010,869 B1 | 3/2006 | Ellis, III |
| 2002/0133973 A1 | 9/2002 | Lin |
| 2003/0009308 A1 | 1/2003 | Kirtley |
| 2003/0069714 A1 | 4/2003 | Wigley et al. |
| 2003/0182055 A1* | 9/2003 | Curatolo et al. ............. 701/207 |
| 2004/0118831 A1 | 6/2004 | Martin |
| 2005/0046139 A1 | 3/2005 | Guan |
| 2005/0060906 A1 | 3/2005 | Zimerfeld |
| 2005/0235523 A1 | 10/2005 | Flechsig et al. |
| 2005/0245839 A1 | 11/2005 | Stivoric et al. |
| 2005/0261609 A1 | 11/2005 | Collings et al. |
| 2006/0001545 A1 | 1/2006 | Wolf |
| 2006/0030783 A1 | 2/2006 | Tsai et al. |
| 2006/0046907 A1 | 3/2006 | Rastegar et al. |
| 2006/0100546 A1 | 5/2006 | Silk |
| 2006/0195050 A1 | 8/2006 | Alwan et al. |
| 2007/0021689 A1 | 1/2007 | Stergiou et al. |
| 2007/0173903 A1 | 7/2007 | Goren et al. |

FOREIGN PATENT DOCUMENTS

| | | |
|---|---|---|
| EP | 0877346 B1 | 9/2001 |
| EP | 1 293 140 A2 | 3/2003 |
| WO | WO 2005/037103 A1 | 4/2005 |

OTHER PUBLICATIONS

Anderson, K.A. (2003) "An Intelligent Insole for Diabetic Patients with the Loss of Protective Sensation," Thesis.

Armstrong et al.(1996) "Monitoring Neuropathic Ulcer Healing with Infrared Dermal Thermometry," *J. Foot Ankle Surg.* 35(4):335-338.

Armstrong et al. (Jul. 1997) "Monitoring Healing of Acute Charcot's Arthropathy with Infrared Dermal Thermometry," *J. Rehab. Res. Dev.* 34(3):317-321.

Armstrong et al. (1997) "Infrared Dermal Thermometry for the High-Risk Diabetic Foot," *Phys. Ther.* 77(2):169-177.

Benbow et al. (1994) "The Prediction of Diabetic Neuropathic Plantar Foot Ulceration by Liquid-Crystal Contact Thermography," *Diabetes Care* 17(8):835-839.

Boyko et al. (2001) "Skin Temperature in the Neuropathic Diabetic Foot," *J. Diabetes Complications* 15(5):260-264.

Chu et al. (Apr. 1990) "Neural Networks for System Identification," *IEEE Control Systems Magazine* 10(3):31-35.

Duffin, A. (1999) "New Approach to Reducing High Plantar Pressures in Adolescents with Diabetes," *Clin. Biomech.* 14(8):553.

Fairburn et al. (1999) "Routine Use if Dynamic Plantar Pressure Measurement in the Treatment of Diabetic Transtibial Amputees," *Clin. Biomech.* 14(8):553-554.

Jernberger, A. (1993) "The Neuropathic Foot," *Prosthetics Orthotics Int.* 17(3):189-195.

Lord et al. (2000) "A Study of In-Shoe Plantar Shear in Patients with Diabetic Neuropathy," *Clin. Biomech.* 15:278-283.

Manhanty et al. (1981) "Thermal Response of Paraplegic Skin to the Application of Localized Pressure," *Arch. Phys. Med. Rehab.* 62(12):608-611.

Manley et al. (1980) "Repetitive Mechanical Stress and Denervation in Plantar Ulcer Pathogenesis in Rats," *Arch. Phys. Med. Rehab.* 61:171-177.

Morley et al. (Jul. 2001) "In-Shoe Multisensory Data Acquisition System," *IEEE Trans. Biomed. Eng.* 48(7):815-820.

Mueller et al. (1999) "Use of Computed Tomography and Plantar Pressure Measurement for Management of Neuropathic Ulcers in Patients with Diabetes," *Phys. Ther.* 79(3):296-307.

Pinzur et al. (1999) "American Orthopedic Foot and Ankle Society Shoe Survey of Diabetic Patients" *Foot Ankle Int.* 20(11):703-707.

Pinzur, M.S. (Dec. 1999) "American Orthopaedic Foot and Ankle Society Diabetic Shoe Survey," *Diabetes Care* 22(12):2099-2100.

Pitei et al. (1999) "Plantar Pressures are Elevated in the Neuroischemic and the Neuropathic Diabetic Foot," *Diabetes Care* 22(12):1966-1970.

Ramsey et al. (1999) "Incidence, Outcomes, and Cost of Foot Ulcers in Patients with Diabetes," *Diabetes Care* 22(3):382-387.

Richer et al. (1999) "In-Shoe Multisensory Data Acquisition," Proceedings of the First Joint BMES/EMBS Conference, 1999 IEEE Engineering in Medicine and Biology 21$^{st}$ Annual Conference and the 199 Annual Fall Meeting of the Biomedical Engineering Society 1:618.

Romig, T.S. (2000) "Neuro-Fuzzy Based Artificial Sensation System for the Early Detection of Diabetic Foot Pathology," Thesis.

Shoureshi et al. (1995)) "Intelligent Control and Actuators for Structures," *J. Smart Mater. Struct.* 4:A132-A139.

Shourechi, R.A. (Jul. 1996) "Intelligent Control Systems," Track Q No. 6, 1006 World Cong. Symposium Panel.

Shoureshi, R.A. (Jun. 1993) "Intelligent Control Systems: Are They for Real," *ASME J. Dynamic Systems Measure. Control* 115(2B):392-400.

Stess et al. (1997) "The Role of Dynamic Plantar Pressures in Diabetic Foot Ulcers," *Diabetes Care* 20(5):855-858.

Tomas et al. (Apr. 2000) "The Diabetic Foot," *British J. Radiol.* 73(868):443-450.

Ward et al. (1999) "Foot Education Improves Knowledge and Satisfaction Among Patients at High Risk for Diabetic Foot Ulcer," *Diabetes Education* 25(4):560-567.

International Search Report, International Application No. PCT/US07/83579, Oct. 6, 2008, 2 pages.

S. R. Chu et al., "A Hopfield-Based Neuro-Diagnostic System," Proceedings of the Am. Control Conference, Chicago IL, Jun. 1992, pp. 2629-2633.

Diaz et all. (2004) "Preliminary Evaluation of a Full-Time Falling Monitor for the Elderly," *Ann. Int. Conf. Eng. Med. Biol. Proc.* 26(3):2180-2183.

Donaghue et al. (1997) "Foot Pressure Measurement," *Orthapaedic Phys. Ther. Clinics North Am.* 6(1):1-16.

F-Scan VersaTek System, http://www.tekscan.com/medical/system-fscan1.html, Downloaded Nov. 15, 2007.

Hwang et al. (2004) "Development of Novel Algorithm and Real-Time Monitoring Ambulatory System Using Bluetooth Module for Fall Detection in the Elderly," *Ann. Int. Conf. IEEE Eng. Biol. Proc.* 26(3):2204-2207.

Kadono et al. (2003) "Plantar Pressure Distribution Under the Forefoot with Hallux Valgus During Walking," *J. Nara Med. Assoc.* 54(5-6):273-281 (Abstract Only).

Kirtley, C. (Feb. 2001) "Gait Analysis from the Ground Up," *Rehab Management* http://www.rehabpub.com/Itrehab/22001/4.asp, Downloaded Nov. 15, 2007.

Kirtley (2001) "An Instrumented Insole for Kinematic and Kinetic Gait Measurements," Proc. of the 5$^{th}$ Symposium on Footwear, Biomechanics, Zurich, Switzerland, pp. 52-53.

Mathie et al. (pr. 2004) "Accelerometry: Providing an Integrated, Practical Method for Long-term Ambulatory Monitoring of Human Movement," *Phys. Measur.* 25(2):R1-R20.

Morris et al. (2003) "A Compact Wearable Sensor Package for Clinical Gait Monitoring," *Offspring* 1(1):7-15.

Najafi et al. (2000) "Falling Risk Evaluation in Elderly Using Miniature Gyroscope," *1$^{st}$ Ann. Int. IEEE-EMBS Special Top. Conf. Microtechnol. Med. Biol. Proc.*:557-561.

Pappas et al. (2004) "A Reliable Gyroscope-Based Gait-Phase Detection Sensor Embedded in a Shoe Insole," *IEEE Sensors J.* 4(2):268-274.

Pappas et al. (2001) "A Reliable Gait Phase Detection System," *IEEE Trans. Neural Syst. Rehabil. Eng.* P(2):113-125.

Pitei et al. (1999) "Plantar Pressures are Elevated in the Neuroschemic and the Neuropathic Diabetic Foot," *Diabetes Care* 22(12):1966-1970.

Popovic et al. "Gait Identification and Recognition Sensor," http://www.ifess.org/vienna98/session07/Popovic%20M.pdf, Sep. 22-24, 1998.

Prado et al. (2002) "Distributed Intelligent Architecture for Falling Detection and Physical Activity Analysis in the Elderly," *Ann. Int. Conf. IEEE Eng. Med. Biol. Proc.* 3:1910-1911.

Surdilovic et al. (2004) "Gait Phase and Centre of Pressure Measuring System," *2nd IEEE Int. Conf. Indust. Informatics* :331-334.

International Search Report, International Application No. PCT/US2007/083575, May 15, 2008, 2 pages.

Office Action in U.S. Appl. No. 11/556,858 mailed Feb. 22, 2008, 10 pages.

Office Action in U.S. Appl. No. 11/556,858 mailed Nov. 7, 2008, 9 pages.

Office Action in U.S. Appl. No. 12/435,529 mailed Jul. 7, 2009, 10 pages.

* cited by examiner

F : Fuzzification, N : Normalization
D : Defuzzification, Σ : Summation

SMART INSOLE FOR DIABETIC PATIENTS

BACKGROUND OF THE INVENTION

There are almost 16 million patients with diabetes in the United States; approximately 798,000 new cases are diagnosed each year (1). Among people with diabetes, 15% will experience a foot ulcer in their lifetime. Foot ulcers are a major predictor of future lower-extremity amputation in patients with diabetes. One of the many dangers of pedal ulcers is that they are portals of entry for infection and directly overlie more than 90% of cases of pedal osteomyelitis (a destructive bone disease) (2). About 14-24% of people with a foot ulcer will require an amputation. It is therefore not surprising that diabetes is the leading cause of non-traumatic lower-extremity amputations in the US. Despite much effort directed toward amputation prevention in the last decade, the incidence of lower-extremity amputation in people with diabetes continues to rise (3). The cost of diabetic foot ulcers is at least $1 billion annually in the United States (4). In a study done by Ramsey, S. D. et al at the Group Health Cooperative of Puget Sound, the attributable cost associated with a foot ulcer was $28,000.00 per patient in the two years following diagnosis (5).

Unfortunately, the mortality rate for amputees is very high and constantly increasing. If there were a diagnostic tool that could be used as a warning device for those patients that suffer from the loss of protective sensation caused by peripheral neuropathy, many diabetics could return to a more "normal" lifestyle. It is well known that unrecognized trauma has gives rise to most of the foot problems that this group of individuals suffer from. Development of a device that could be used on a daily basis by the patient that would provide the patient with feedback to inform them about when they are at risk would be very valuable.

One of the largest tasks in the development of such a tool is to find what characteristics of diabetic feet are indicators of the condition of the individual's feet. Commonly, pressure has been and remains to be an important indicator of ulceration (6, 7, 8, 9). In-shoe pressure, unfortunately, is a difficult and expensive parameter to measure. There are some pressure-sensing devices available such as the Novel/EMED insoles and the Tekscan F-scan. Neither of these systems meets the desired goal of making the patient completely independent and aware of their foot condition at any time. The Novel insole starts at $10,000.00 for the entry-level variety. The Tekscan insole is cheaper but requires a much more bulky data acquisition system. The Tekscan insoles are designed for a small number of cycles. After a few uses, they lose their ability to accurately determine the pressure.

Temperature, which is very closely associated with pressure, is a much more reliable parameter to measure. This is based, in part, on the available hardware. Thermistors that are highly accurate and also very small are readily available. However, less attention has been paid to plantar temperatures as an indicator of ulcer risk as compared to pressure (10, 11, 12).

U.S. Pat. No. 6,195,921 describes a device that measures pressure of predetermined pressure points of the foot using a flexible sensor mat, and also measures the temperature inside the shoe. U.S. Pat. No. 5,642,096 contains pressure and temperature sensors in a liquid hydrocell within an insole to detect the pressure and temperature values of a patient's feet. U.S. Pat. No. 5,929,332 describes a sensor shoe with a plurality of sensors which measure pressure, temperature, moisture of feet and activates an alarm if values exceed a preset threshold. US patent application 2005/0060906 describes shoes which pump hot air and odor out and fresh air in, which pumps are controlled by an electronic temperature control unit on the outside of the shoe.

Clinically, patients with the loss of protective sensation and failing eyesight are asked to monitor their own feet between visits to their podiatrist. Sadly, many patients are presented to the emergency room after reaching a point of no return in regard to their feet. Currently, there is no device available that can provide a portable and continuous monitoring and assessment of the condition of the feet in diabetic patients. Such a device is urgently needed.

BRIEF SUMMARY OF THE INVENTION

Provided is a system for monitoring parameters of the foot, including temperature. Also provided is a method for monitoring foot temperature, using the system as described herein. More particularly, provided is a system for monitoring foot temperature comprising: a plurality of temperature sensors; an algorithm which compares the data from the temperature sensors to a signature profile, and provides a feedback value; means for communicating the feedback value; and a power source. Another example of the system comprises: a plurality of temperature sensors which generate a signal; a circuit means electrically connected to the plurality of temperature sensors whereby said signal is collected; a transmission means to transmit the signal; a power source electrically connected to said plurality of temperature sensors, circuit means, and transmission means; a software program that receives the transmitted signal and compares the transmitted signal to a signature profile and generates a feedback signal; a feedback means which transmits the feedback signal. Also provided is a method for monitoring foot temperature comprising: collecting signals from one or more temperature sensors located in sensing proximity to a patient's foot, generating a test profile; comparing the test profile to a signature profile; generating a feedback signal; communicating the feedback signal. Also provided is a system for measuring parameters of the foot comprising: one or more sensors selected from the group consisting of: temperature, pressure and humidity; an algorithm which uses the data from the sensors and creates a feedback value; means for communicating the feedback value; and a power source.

In one embodiment, the sensors are located in a shoe, shoe insole, or sock. As used herein, "shoe" indicates a device which at least partially encloses the foot. A shoe may contain attachment devices known in the art such as velcro, laces, or elastic, or other attachment devices known in the art or may be attached to the foot by the use of tape, for example medical tape. As used herein, "shoe insole" or "insole" indicates a structure that may be placed in a shoe or is a part of a shoe, such as a conventional insole known in the art. A shoe insole may also be placed on the foot and attached using any suitable means, such as the use of tape, string, or elastic bands. The use of a separate insole without a shoe may be useful if the patient is unable to be fitted with shoes. The use of any term describing the location of the sensors is intended to encompass the other terms.

The invention is useful for any animal or person that has one or more feet or appendages. The invention is useful for mammals. The invention is useful for humans. The invention is also useful for animals, including horses, cows or dogs, where the temperature profile can be used as an early determiner of illness or injury.

The system can be used in different ways. For example, the system can be used to detect conditions that are likely to result in ulcerations. In one example, the temperature of a particular location of a patient's foot is detected. In another example, the temperature profile of a patient's foot temperature is detected by using more than one temperature sensor in different locations. The patient's temperature or temperature profile is compared to a "signature" value or profile using an algorithm. In one example, a neuro-fuzzy decision-making system is used. The neuro-fuzzy decision-making system uses a learning algorithm to determine its rules by processing data samples. For example, a library of values or profiles is created by measuring the temperature or profiles of people having normal feet or certain disorders. This library creates the "signature" temperature or profile. Other variables can be added to the neuro-fuzzy decision-making system which are designed or used by medical practitioners having experience with foot disorders to take into account other characteristics. This neuro-fuzzy decision making system is described further herein. The algorithm provides a feedback value. The feedback value can be used in many different ways. In one embodiment, the feedback can be communicated to the user. In one example of this embodiment, the user is notified if the test profile is within the normal spatial profile parameters or outside the normal spatial profile parameters. The notification can be visual, audio and/or vibratory feedback, as described elsewhere herein. The user is altered if the condition is safe, warning or dangerous, for example. The feedback can be provided to either the user or a care-giver, for example.

The feedback and/or data from the sensor(s) may be stored on electronic media for future use. This can be useful for medical professionals to review and monitor a patient's activity or disease treatment progress, for example. There are other uses of the invention which will become apparent upon review of the disclosure herein. These uses are intended to be encompassed in this disclosure.

DETAILED DESCRIPTION OF THE INVENTION

The following description contains non-limiting examples which are intended to further illustrate some embodiments of the invention.

This invention is a temperature-based smart insole capable of continuously or intermittently measuring the foot temperature of the patient at one or more locations of the foot while the insole is worn. The ambient shoe temperature may also be monitored. This allows normalization of all temperatures before creating a temperature profile, which can be used in one embodiment for application in the neuro-fuzzy network. The device provides feedback to the patient alerting the individual of risk based on his/her plantar temperatures. Benefits of this device include: its ability to free the patient from the clinical setting and increase patient's confidence to be mobile, thus enhancing circulation while at the same time allowing the patient to self-monitor their feet. For example, diabetic patients with peripheral neuropathy can wear the insoles and be automatically alerted when their foot temperature has exceeded a profile, designed within the insole's intelligence. In addition, such a device provides higher degrees of mobility for diabetic patients. Many persons with diabetes would like to exercise but are afraid of damaging their feet. The smart insole provided herein, with its continuous monitoring, would allow such people to be active and perform exercises so long as the insole does not detect any potential danger.

Foot diseases or disorders other than ulceration are known to cause a foot temperature change. Some foot diseases or disorders cause an increase in temperature at certain locations of the foot. For example, a common precursor to Charcot foot (a sudden softening of the bones in the foot that can occur in people who have significant nerve damage) is an increase in temperature. Therefore, a device that monitors temperature changes of the foot could be used as an indicator for active Charcot foot disease. Other foot diseases or disorders cause a decrease in temperature at certain locations of the foot. Other foot diseases or disorders cause an increase in the overall temperature of the foot. Other foot diseases or disorders cause a decrease in the overall temperature of the foot. The invention described here can be used to diagnose or monitor these diseases or disorders using the methods described herein.

Figure 1:
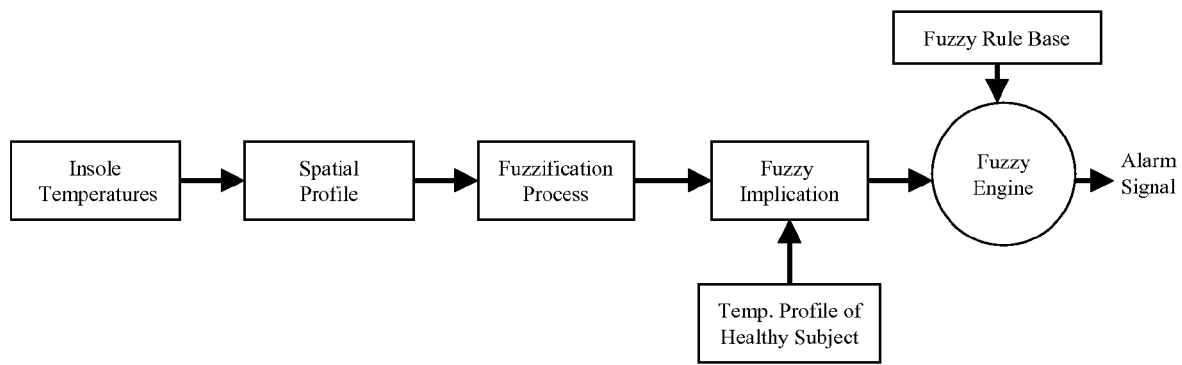
FIG. 1 shows an exemplary block diagram of the operation of the insole.

The smart insole comprises one or more temperature sensors placed at one or more locations in the insole. A temperature sensor that measures the ambient temperature, as discussed above, may also be used. It is preferred the temperature sensors are embedded in the insole so the user's activity is not affected by the sensors. FIG. 1 illustrates one embodiment of the operation of the invention. The temperature of the insole is measured by the temperature sensors. Based on the temperature readings from strategic locations of the foot, a spatial temperature profile of the foot is developed. This spatial temperature profile is fuzzified and compared with the signature profile of a healthy individual (or other signature profile, as desired), using fuzzy implications. Based on a fuzzy inference engine, the insole makes a decision on whether to alert the patient. The alert signal is transmitted in various ways, as described further herein.

The temperature sensors may be any suitable temperature sensor, as known in the art. One suitable temperature sensor is a Thermometrics thermistor, or a Fenwal thermistor. If is preferred that the temperature sensor(s) be moisture resistant. There are other temperature sensors that are useful in the invention. A combination of temperature sensors may be used. In one embodiment, there is a plurality of temperature sensors. In one embodiment, the temperature sensors are located in sensing communication with different parts of the foot. The different parts of the foot may include one or more of: big toe pad, heel, under one or more metatarsals, inner ball, outer ball, and outside edge. The temperature sensors may be different sizes, depending on the location or other factors, as known in the art. There may be as many or as few temperature sensors as desired to obtain the desired sensitivity of measurement, as balanced by cost, durability and other factors as known in the art. In different embodiments, there are one, two, three, four, five, six, seven, eight, nine or ten temperature sensors. In one embodiment, there are more than ten temperature sensors. In one embodiment, there are less than ten temperature sensors. In one embodiment, there are less than five temperature sensors. In one embodiment, there are five or fewer temperature sensors. In one embodiment, there are more than two temperature sensors. In one embodiment, there is more than one temperature sensor. All individual values and ranges are intended to be included to the extent as if they were individually listed. In one embodiment, the temperature sensors do not cover a substantial portion of the user's foot. In one embodiment, the temperature sensors are not arranged in an array. In one embodiment, there is at least one temperature sensor in an area other than the periphery of the shoe.

The insole may also comprise one or more pressure sensors. If used, the pressure sensor may be any suitable pressure sensor, as known in the art. One suitable example is the FlexiForce, obtained by Teskan, South Boston, Mass. There are other pressure sensors that are useful in the invention. A combination of pressure sensors may be used. In one embodiment, there is a plurality of pressure sensors. In one embodiment, the pressure sensors are located in pressure communication with different parts of the foot. The different parts of the foot may include one or more of: big toe pad, heel, under one or more metatarsals, inner ball, outer ball, and outside edge. The pressure sensors may be different sizes, depending on the location or other factors, as known in the art. There may be as many or as few pressure sensors as desired to obtain the desired sensitivity of measurement, as balanced by cost, durability and other factors as known in the art. In different embodiments, there are one, two, three, four, five, six, seven, eight, nine or ten pressure sensors. In one embodiment, there are more than ten pressure sensors. In one embodiment, there are less than ten pressure sensors. In one embodiment, there are less than five pressure sensors. In one embodiment, there are five or fewer pressure sensors. In one embodiment, there are more than two pressure sensors. All individual values and ranges are intended to be included to the extent as if they were individually listed. In one embodiment, the pressure sensors do not cover a substantial portion of the user's foot. In one embodiment, the pressure sensors are not arranged in an array. In one embodiment, there are no pressure sensors in the insole.

Although temperature is particularly mentioned in examples herein, there are several useful combinations of sensors that are also intended to be included in this description. For example, temperature only may be measured. Temperature and pressure may be measured. Temperature and humidity may be measured. Temperature, pressure and humidity may be measured. As known in the art, there are many suitable humidity sensors that may be used. Any combination of temperature, and pressure and/or humidity sensors may be used in any desirable arrangement to create the desired profile. All embodiments and features mentioned herein may be used with any combination of sensors.

Figure 5:
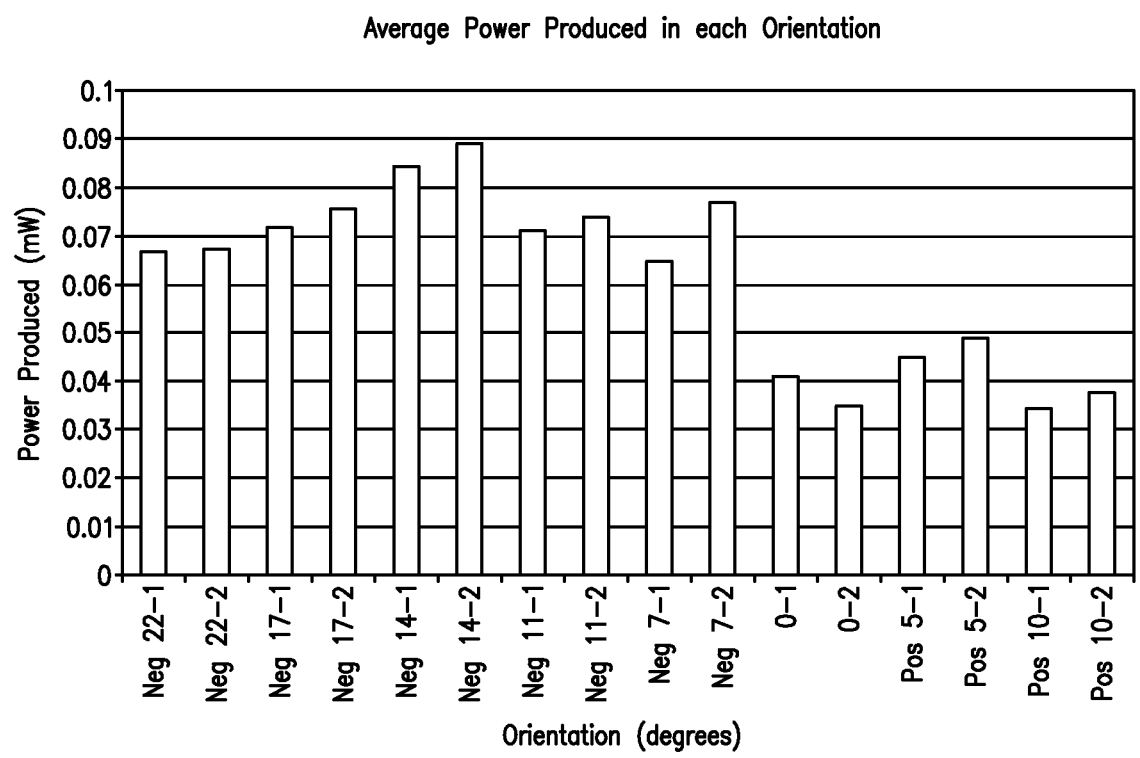
FIG. 5 shows exemplary power produced from knee joint orientation.

The system can be powered by any suitable energy source. The power source can be one or more of: kinetic energy (energy generated by the user walking); and alternating or direct current, including one or more batteries which may be rechargeable or non-rechargeable. In one embodiment, there is a combination of energy sources used. Different portions of the system can be powered in different ways. For example, the portions of the system that are present in the shoe, shoe insole or sock may be powered by kinetic energy, while the other portions of the system are powered by alternating current. As shown in FIG. 5, power can be generated from knee joint kinetic energy. This can be used to drive the shoe insole. Alternatively, the portions of the system that are present in the shoe, shoe insole or sock may be powered by batteries. In a portable system, it is desired that no parts of the system require wall current.

The alert signal(s) (or feedback value) can be transmitted or displayed in various ways. In one embodiment, the alert signals are communicated by a method selected from the group consisting of: visual indication, tactile indication, audible indication and combinations thereof. Visual indication can include different colored lights which correspond to various alert conditions. For example: green can be used to indicate the foot status is safe, yellow can be used to indicate the foot status requires caution, and red can be used to indicate the foot status is potentially dangerous and the behavior should be stopped and the feet examined, or other action taken. These lights may be present in any suitable reporting device. For example, the lights may be incorporated in eyeglasses which the user may wear. The lights may be incorporated in a hand-held device or a device worn around the neck. The lights may be incorporated in a wall-mounted system, for example, in a physician's office or patient room. Audible indication can include different tones and/or volumes of tones to correspond to various feedback conditions. Tactile indication can include a physical sensation presented to the user if a particular feedback condition is present. For example, a system that presents a signal such as a tapping motion can be incorporated in a band worn on a body part such as the wrist or arm, and the system can be designed to send a signal when an unsafe condition is present. The alert signal can be transmitted wirelessly to a pager-type receiver carried by the patient, a caregiver, or a physician's office, for example.

Neuro-Fuzzy Decision Making System

Figure 6:
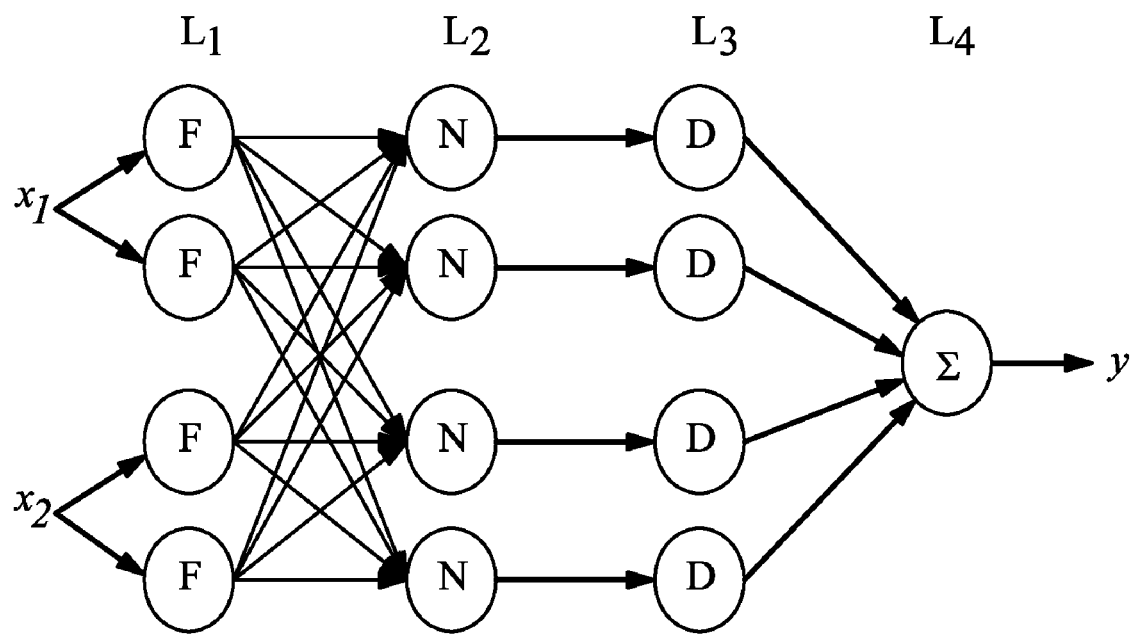
FIG. 6 shows an architecture of the inference engine.

An inference engine that integrates advantages of a neural network and fuzzy logic is incorporated in this system. This neuro-fuzzy inference engine has five layers, in one embodiment, and can be used for any number of inputs and outputs (MIMO). It employs the gradient descent method and the least square estimation (LSE) algorithms to train the network. FIG. 6 shows an architecture of the inference engine.

Layer 1: (Fuzzification layer) Each node generates a membership degree of a linguistic value. The $k^{th}$ node in this layer performs the following operation:

$$O_k^1 = \mu_{A_{ij}}(x_i) = \frac{1}{1 + \left(\frac{x_i - a_{ij}}{b_{ij}}\right)^2} \tag{8}$$

Layer 2: (Multiplication Layer) Each node calculates the firing strength of each rule by using multiplication operation.

$$O_k^2 = \prod_i O_{ij}^1(x_i) \quad (1 \le k \le 4) \tag{9}$$

Layer 3: (Normalization layer) The number of nodes in this layer is the same as the first layer, where the output of layer two is determined according to:

$$O_k^3 = \frac{O_k^2}{\sum_k O_k^2} \quad (1 \le k \le 4) \tag{10}$$

Layer 4: (Defuzzification layer) The number of nodes in this layer is equal to the number of nodes in layer one times the number of outputs. The defuzzified value for the $$y_k = \begin{cases} c_k - d_k \sqrt{\dfrac{1}{O_k^3} - 1} & \text{if } k = \text{odd} \\ c_k + d_k \sqrt{\dfrac{1}{O_k^3} - 1} & \text{if } k = \text{even} \end{cases} \quad (1 \le k \le 4) \tag{11}$$

where $\{c_k, d_k\}$ are consequent parameters and are used to adjust the shape of the membership function of the consequent part. Then, the output of this layer becomes:

$$O_k^4 = O_k^3 \cdot y_k = \begin{cases} O_k^3 \cdot \left(c_k - d_k \sqrt{\dfrac{1}{O_k^3} - 1}\right) & \text{if } k = \text{odd} \\ O_k^3 \cdot \left(c_k + d_k \sqrt{\dfrac{1}{O_k^3} - 1}\right) & \text{if } k = \text{even} \end{cases} \quad (1 \le k \le 4) \tag{12}$$

Layer 5: (Summation layer) Here, the number of nodes is equal to the number of outputs. There is only one connection between each node in layer three and a node in the output layer:

$$O_1^5 = \sum_k O_k^4 \quad (1 \le k \le 4) \tag{13}$$

In the training process, the engine tries to find the minimizing error function between target value and the network output. For a given training data set with P entries, the error function is defined as:

$$E = \sum_{p=1}^{P} E_p = \frac{1}{2} \sum_{p=1}^{P} (T_p - O_{1,p}^5)^2, \quad (1 \le p \le P). \tag{14}$$

There are several key attributes of this neuro-fuzzy inference engine that adapt it well for the present invention:

(a) it uses a combination of a fuzzy inference engine and an adaptive neural network (b) it uses fuzzy reasoning for both fuzzification and defuzzification, that is, the membership functions are half of a bell-shape function called monotonic nonlinear functions (c) it can be applicable to Multi-input and Multi-output (MIMO) system (d) it uses associated hybrid learning algorithm to tune the parameters of membership functions: Feedforward Process; Least Square Estimation; Backward Process; Gradient Descent method (e) it uses an optimal learning rate that is updated after each learning process (f) it has the least number of coefficient to learn, has a fast convergence rate, and is therefore suitable for real-time applications.

This inference engine can be used in modeling and mapping of uncertain systems whose mathematical representation (e.g. differential equations) is not available to predict its future behavior. It integrates the best features of a fuzzy system (fuzzy reasoning) and neural networks (learning). Neuro-fuzzy inference technique provides a means for the fuzzy modeling to learn information about a data set, which will compute and generate the membership function parameters, so that the associated fuzzy inference system can track the given input and output pattern. Its learning method works similarly to that of neural networks. This network can be used to find out system parameters and unknown factors through the training process, which means it achieves the goal of system identification.

Both healthy populations and target populations have variations in the foot temperature profiles. This underscores the importance of the fuzzy logic control used here. For the fuzzy inference made in this system, input variables may include temperature readings, ambient temperature and rate of change of temperatures. The fuzzy output is the degree of certainty about the occurrence of a problem with the feet, for example, the occurrence of an ulceration. Therefore, instead of using a temperature threshold, a rule-based decision system is used. This allows input of the physician's knowledge and diagnosis pattern into the operation of this smart insole.

A set of rules is developed for the output. For the case of foot ulceration, these rules are of the form:

If temperature is low and temperature rate of change is low, then condition is safe.

If temperature is medium and temperature rate of change is low, then condition is warning.

If temperature is high and temperature rate of change is high, then condition is dangerous.

Figure 4:
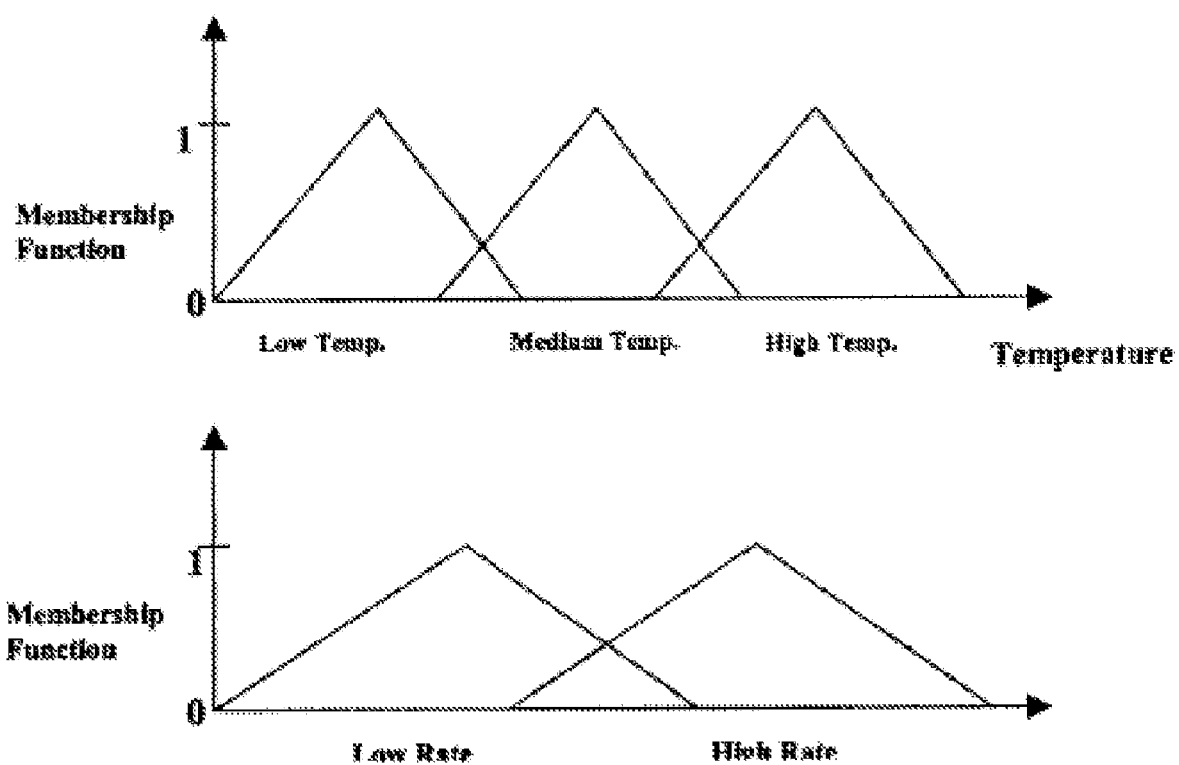
FIG. 4 shows exemplary rule-based result values.

These rules are shown in FIG. 4, where the top figure shows the membership function for temperature data based on the temperature of a certain location of the foot, or the temperature profile of the insole. The bottom figure shows the membership function for rate of change of temperature. Other rules may be used to monitor different functions, as determined by the programming of the fuzzy logic. This programming is well known by one of ordinary skill in the art.

For other disorders, the rules may change. These changes are easily incorporated into the decision making process. The insole can be used to diagnose or monitor many different disorders by changing the programming, as known in the art. In one example, the patient's noninjured or diseased foot is used as the signature profile or value. By using diagnostic information, one can train the neural network and thereby incorporate the rules as part of the neuro-fuzzy inference engine.

Exemplary Insole Fabrication

Figure 2A:
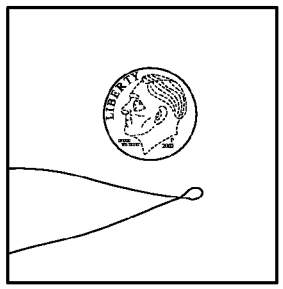
FIG. 2 shows an example of embedding thermistors.
Figure 2B:
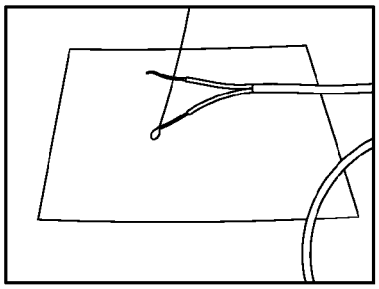
Figure 2C:
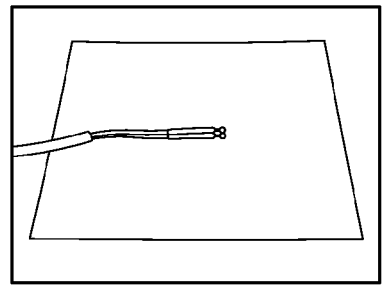
Figure 2D:
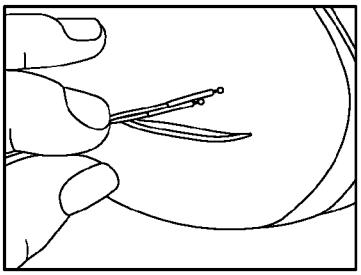
Figure 2E:
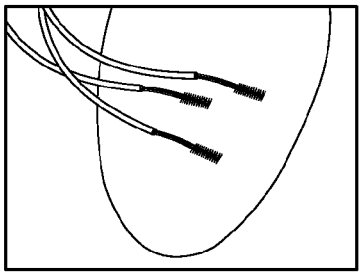
Figure 2F:
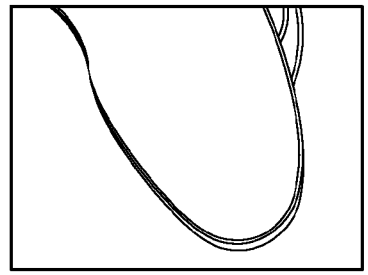

The Thermometrics thermistor MC65F103B is an epoxy-coated thermistor with a maximum diameter of 0.065 inches (0.165 cm). The Fenwal thermistor has a maximum diameter of 0.95 inches (0.241 cm) and is also epoxy-coated. The leads of the thermistors are soldered to a twisted pair wire that would run under the insole and out the side of the shoe. For this example, seven thermistors are embedded within each insole. The strategic locations for the thermistors are: under the metatarsal heads, the heel, and the hallux. FIG. 2 pictorially displays the installation process of the thermistor into the insole. FIG. 2A shows the size of one thermistor. FIG. 2B and 2C show the wiring of a thermistor. FIG. 2D shows one example of insertion of the thermistor. FIG. 2E shows placing several thermistors in desired locations of the insole. FIG. 2F shows the completed insole.

Clinical Results

To assess the operation of this smart insole, human subject trials were conducted. A total of sixty-nine patients signed a consent form and sixty patients successfully completed the clinical trial. Most of the volunteers were Caucasian males (n=47), with the remaining males being Hispanic (n=4), African American (n=4), and Asian (n=1). There were only 4 females—all Caucasian. The mean and standard deviations of ages for each group was: Control 33.3 (±15.14), Diabetic 69.6 (±10.21), and Neuropathic 66.8 (±12.71).

Figure 3:
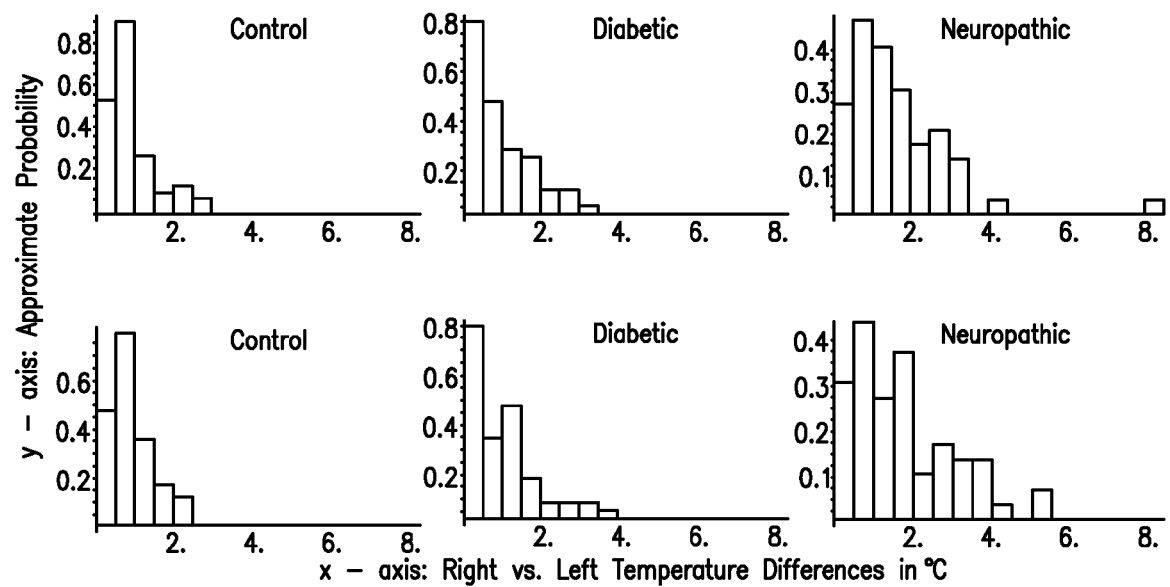
FIG. 3 shows histograms of the maximum temperature differences (in °C.) noted at the hallux during the last five minutes of sitting data collection (top row) and the last five minutes of walking data collection (bottom row).

FIG. 3 shows a sample of histograms for the hallux of left and right foot. Examination of the histograms shows the control group to commonly experience differences of up to 2° C. during sitting. These histograms have been shown as approximate probability density functions of the right vs. left temperature data. The neuropathic group shows common differences as high as 3-3.5° C. During walking it becomes more common across all groups to see increased frequency of high temperature differences.

From the Tukey tests, above, it has been observed that very clear differences in sitting temperatures between these groups exist. This is in accordance with previously published literature stating that there are temperature differences between neuropathic feet and other feet. These findings do confirm the results of Boyko et al. that found neuropathic patients have cooler feet than healthy patients. These tests have been successful on all fronts. The temperature control of the contralateral foot has been shown to be more variant than previously thought by some researchers. This is, to our knowledge, has been the first clinical trial to record such measurements. The temperature profiles of these patients is stored in the database of the smart insole. From these profiles, a fuzzy rule-based inference engine is developed for comparison of temperature profiles of different categories of patients, as described earlier herein. Additional temperature profiles can be added to the database. For decision-making, either the entire temperature profile can be used, or the temperature reading at one or more locations of the foot. Temperature profiles can be given as an input vector to the neuro-fuzzy inference engine with the output being diagnostic results.

REFERENCES

1. Pinzur, M. S.; Shields, N. N.; Goelitz, B.; Slovenkai, M.; Kaye, R.; Ross, S. D.; Suri, M. "American Orthopaedic Foot and Ankle Society Shoe Survey of Diabetic Patients" Foot and Ankle International 20(11):703-7, 1999
2. Tomas, M. B.; Patel, M.; Marwin, S. E.; and Palestro, C. J. "The diabetic foot" British Journal of Radiology 73(868): 443-50, April 2000
3. American Diabetes Association: Consensus Development Conference Report. April 1999, Boston, Mass.
4. Ward, A.; Metz, L.; Oddone, E. Z.; Edelman, D. "Foot Education Improves Knowledge and Satisfaction Among Patients at High Risk for Diabetic Foot Ulcer." Diabetes Education 25(4):560-67, July-August 1999
5. Ramsey, S. D.; Newton, K; Blough, D; McCulloch, D K; Sandhu, N; Reiber, G E; Wagner, E H "Incidence, Outcomes, and Cost of Foot Ulcers in Patients with Diabetes" Diabetes Care 22(3):382-87, 1999
6. Manley, M. T. and Darby, T. "Repetitive Mechanical Stress and Denervation in Plantar Ulcer Pathogenesis in Rats." The Archives of Physical and Medical Rehabilitation 51:171-75, 1980
7. Mueller, M J; Smith, K E; Commean, P K; Robertson, D D; Johnson, J E "Use of computed tomagraphy and plantar pressure measurement for management of neuropathic ulcers in patients with diabetes" Physical Therapy 79(3): 269-307, 1999
8. Pitei, D L; Lord, M; Foster, A; Wilson, S; Watkins, P J; Edmonds, M E "Plantar pressures are elevated in the neuroischemic and the neuropathic diabetic foot" Diabetes Care 22(12):1966-1970, 1999
9. Stess, R M; Jensen, S R; Mirmiran, R "The role of dynamic plantar pressures in diabetic foot ulcers" Diabetes Care 20(5):855-58, 1997
10. Armstrong, D. G.; Lavery, L. A.; Liswood, P. J.; Todd, W. F.; Tredwell, J. A.; and Birk, J. "Infrared dermal thermometry for the high-risk diabetic foot" Physical Therapy 77(2):169-180, 1997
11. Benbow, S. J.; Chan, A. W.; Bowsher, D. R.; Williams, G.; Macfarlane, I. A. "The prediction of diabetic neuropathic plantar foot ulceration by liquid-crystal contact thermography." Diabetes Care 17(8):835-9, 1994
12. Armstrong, D. G. and Lavery, L. A. "Monitoring neuropathic ulcer healing with infrared dermal thermometry." Journal of Foot and Ankle International 35(4):335-8, 1996

Although the description herein contains many specificities, these should not be construed as limiting the scope of the invention, but as merely providing illustrations of some of the embodiments of the invention. Thus, additional embodiments are within the scope of the invention and within the following claims. All references cited herein are hereby incorporated by reference to the extent that there is no inconsistency with the disclosure of this specification. Some references provided herein are incorporated by reference herein to provide details concerning additional methods of analysis and additional uses of the invention.

When a Markush group or other grouping is used herein, all individual members of the group and all combinations and subcombinations possible of the group are intended to be individually included in the disclosure. Every combination of components described or exemplified can be used to practice the invention, unless otherwise stated. One of ordinary skill in the art will appreciate that methods, device elements, and components other than those specifically exemplified can be employed in the practice of the invention without resort to undue experimentation. All art-known functional equivalents, of any such methods, device elements, and components are intended to be included in this invention. Whenever a range is given in the specification, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of elements of a device, is understood to encompass those methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art. The definitions are provided to clarify their specific use in the context of the invention.

We claim:

1. A system for monitoring foot temperature comprising:
   (a) a plurality of temperature sensors located in a shoe or shoe insole, which sensors generate a spatial temperature profile of the foot;
   (b) a neuro-fuzzy decision making algorithm which compares the spatial temperature profile from the temperature sensors to a signature profile, and provides a feedback value;
   (c) means for communicating the feedback value; and
   (d) a power source.

2. The system of claim 1, wherein the means for communicating the feedback value is selected from the group consisting of: visual indication, tactile indication, audible indication and combinations thereof.

3. The system of claim 1, wherein the plurality of temperature sensors is located in a shoe, shoe insole, or sock.

4. The system of claim 1, further comprising a pressure sensor.

5. The system of claim 1, further comprising a humidity sensor.

6. The system of claim 1, comprising temperature sensors in sensing communication with different parts of the foot.

7. The system of claim 1, comprising less than 10 temperature sensors.

8. The system of claim 1, comprising more than 2 temperature sensors.

9. The system of claim 1, wherein the power source is kinetic energy.

10. The system of claim 1, wherein the power source is alternating or direct current.

11. The system of claim 1, wherein the power source is one or more batteries.

12. A system for monitoring foot temperature comprising:
    (a) a plurality of temperature sensors which generate a spatial temperature profile signal, said sensors located in a shoe or shoe insole;
    (b) a circuit means electrically connected to the plurality of temperature sensors whereby said signal is collected;
    (c) a transmission means to transmit the signal;
    (d) a power source electrically connected to said plurality of temperature sensors, circuit means, and transmission means;
    (e) a software program that includes a neuro-fuzzy decision making system that receives the transmitted signal and compares the transmitted signal to a signature profile and generates a feedback signal;
    (f) a feedback means which transmits the feedback signal.

13. The system of claim 12, wherein the feedback means is selected from the group consisting of: visual indication, tactile indication, audible indication and combinations thereof.

14. The system of claim 12, wherein the temperature sensors are located in a shoe, shoe insole, or sock.

15. The system of claim 12, wherein the temperature sensors are located in sensing communication with different parts of the foot.

16. The system of claim 12, comprising less than 10 temperature sensors.

17. The system of claim 12, comprising more than 2 temperature sensors.

18. The system of claim 12, further comprising a humidity sensor.

19. The system of claim 12, further comprising a pressure sensor.

20. The system of claim 12, wherein the power source is kinetic energy.

21. The system of claim 12, wherein the power source is alternating or direct current.

22. The system of claim 12, wherein the power source is one or more batteries.

23. A system for measuring parameters of the foot comprising:
    (a) one or more sensors selected from the group consisting of: temperature, pressure and humidity located in a shoe or shoe insole, wherein the one or more temperature sensors generate a spatial temperature profile of the foot;
    (b) a neuro-fuzzy decision making algorithm which uses the spatial temperature profile from the sensors and creates a feedback value;
    (c) means for communicating the feedback value; and
    (d) a power source.

24. A method for monitoring foot parameters comprising:
    providing one or more sensors located in sensing proximity to a patient's foot;
    collecting signals from said one or more sensors using a circuit means, generating a spatial temperature test profile;
    comparing the test profile to a signature profile using a neuro-fuzzy decision making system;
    generating a feedback signal;
    communicating the feedback signal.

25. The method of claim 24, wherein the sensors are selected from the group consisting of: temperature, pressure and humidity.

26. The method of claim 24, wherein the communicating step is one or more of: visual, tactile, and audible.

* * * * *